United States Patent [19]

Sarstedt

[11] 4,057,050
[45] Nov. 8, 1977

[54] DEVICES FOR EXTRACTING BLOOD

[76] Inventor: Walter Sarstedt, 5223 Numbrecht, Rommelsdorf, Germany

[21] Appl. No.: 635,779

[22] Filed: Nov. 26, 1975

[30] Foreign Application Priority Data

Nov. 29, 1974  Germany .............................. 2456561
July 25, 1975  Germany .............................. 2533256

[51] Int. Cl.$^2$ ...................... A61M 5/315; A61M 1/00
[52] U.S. Cl. ..................................... 128/2 F; 128/234; 128/247; 222/386
[58] Field of Search ............... 128/2 F, 218 R, 218 P, 128/218 PA, 219, 220, 221, 234, 235, 247, 237, 238, 272, 261, 276, 278, DIG. 5, 239; 222/386, 387, 326, 327, 391, 158, 386.5, 341, 498; 141/27; 206/364; 23/258.5; 215/321, 317, DIG. 3

[56] References Cited

U.S. PATENT DOCUMENTS

| 453,322 | 6/1891 | Beekman | 128/235 |
|---|---|---|---|
| 577,682 | 2/1897 | Eissner | 128/234 |
| 729,011 | 5/1903 | Tagliabue et al. | 128/219 |
| 1,074,965 | 10/1913 | McClellan | 128/234 |
| 1,110,189 | 9/1914 | Dodge | 128/234 |
| 1,450,016 | 3/1923 | Bruce | 128/234 |
| 1,521,890 | 1/1925 | Klein | 128/219 |
| 2,218,899 | 10/1940 | Warren | 141/27 X |
| 2,688,325 | 9/1954 | Lockhart | 128/218 P |
| 2,895,773 | 7/1959 | McConnaughey | 128/219 X |
| 3,176,595 | 4/1965 | Schwartz | 128/218 P |
| 3,214,069 | 10/1965 | Dike | 222/498 |
| 3,236,268 | 2/1966 | Simpson | 222/386 |
| 3,263,874 | 8/1966 | Porter et al. | 222/498 |
| 3,486,503 | 12/1969 | Porter et al. | 128/247 X |
| 3,577,980 | 5/1971 | Cohen | 128/2 F |
| 3,754,644 | 8/1973 | Hampel | 128/218 R |
| 3,794,221 | 2/1974 | Hostettler | 222/386 X |
| 3,834,387 | 9/1974 | Brown | 128/218 P |
| 3,855,997 | 12/1974 | Sauer | 128/2 F |
| 3,937,211 | 2/1976 | Merten | 128/218 P |
| 3,958,570 | 5/1976 | Vogelman et al. | 128/234 X |

FOREIGN PATENT DOCUMENTS

| 1,247,644 | 10/1960 | France | 128/218 P |
|---|---|---|---|
| 2,025,379 | 12/1971 | Germany | 128/218 P |
| 1,491,662 | 8/1969 | Germany | 128/218 R |
| 347,472 | 1948 | Italy | 128/235 |

Primary Examiner—J. Reed Fisher
Attorney, Agent, or Firm—Browdy and Neimark

[57] ABSTRACT

Devices for extracting blood which comprises a cylinder having at one end a removable closure member carrying a connection piece for a cannula and an end wall at the other end. A piston is guided in the cylinder in an air-tight manner and a piston rod guided in a central bore in the end wall is releasably attached to an extension of the piston. The end wall forms a rigid stop for the retracted piston and an annular sleeve concentrically surrounding the central bore in the end wall serves for the purpose of receiving and retaining the piston extension, the space between a piston seal and the zone of contact between the extension and annular sleeve being vented when the piston is in its retracted state.

37 Claims, 19 Drawing Figures

DEVICES FOR EXTRACTING BLOOD

The present invention relates to a device for extracting blood which comprises a cylinder having a closure member, carrying the connection piece for a cannula, at one end and an end wall at its other end, and a piston which is guided in the cylinder in an air-tight manner and which has connected thereto a piston rod which is guided in a central bore in the end wall.

Blood extraction devices of this type are known which are also used as syringes or which are primarily used as syringes. The piston rod is generally guided at the other end of the cylinder by means of a transverse wall provided with a central bore and has a handle, or the like, provided at its free end projecting beyond the transverse wall.

When using these known blood extraction devices it is disadvantageous that the blood which has been extracted subsequently has to be transferred from the cylinder into a different vessel, such as a centrifuging tube, for further examination, this being effected by advancing the piston.

However, this renewed movement of the blood which is being extracted constitutes a further mechanical stress on the blood corpuscles and thus increases the risk of haemolysis. Furthermore, the risk of mixing up the blood samples in mass operation in large hospitals is increased, and the work itself is rendered complicated and expensive.

An object of the present invention is to construct a blood extraction device such that its cylinder can be used to store the blood and also to centrifuge the blood after the desired quantity of blood has been drawn off.

According to the present invention there is provided a device for extracting blood which comprises a cylinder having at one end a removable closure member carrying the connection piece for a cannula and an end wall at its other end, and a piston which is guided in the cylinder in an air-tight manner and which has connected thereto a piston rod which is guided in a central bore in the end wall, the end of the piston remote from the closure member having an extension for releasably receiving the piston rod the end wall forming a rigid stop for the retracted piston, an annular sleeve concentrically surrounding the central bore being provided in the end wall for the purpose of receiving and retaining the piston extension, and the space between the piston seal and the zone of contact between the extension and the annular sleeve being vented when the piston is in its retracted state.

After the desired quantity of blood has been extracted, the cannula is removed from the connection piece and the piston is moved up to the rigid stop at the end of the cylinder if this has not already been done. The extension of the piston then enters the annular sleeve surrounding the central bore and is retained therein. The piston rod is then released from the piston. The cylinder containing the blood sample is now reliably sealed at its bottom end. If the blood sample is to be stored or despatched, the connection piece can be closed by means of a cap.

However, if the blood sample is to be centrifuged for the purpose of obtaining the serum, centrifuging can be effected in the same cylinder. In order to remove the serum, the closure member is removed from the cylinder which can then be used in the same manner as the known test tubes or centrifuging tubes.

Preferably, the cylinder is made from a transparent material, particularly plastics material.

The annular sleeve in the end wall and the piston extension are preferably of conical construction in order to retain the extension of the piston when the piston is in its retracted state. The angle of taper is chosen such that self-adhesion is ensured.

In a different preferred construction, the annular sleeve and the piston extension are of cylindrical construction and are provided with a stop bead and a stop groove.

In one embodiment, the end wall of the cylinder is of virtually disc-shaped construction and its side remote from the cylinder is provided with a cylindrical stand ring. Thus, if required, the cylinder can be placed on a table top without a special stand.

In another embodiment, the end wall is of hemispherical construction. After the piston rod and the closure member have been removed, the cylinder then has the external configuration of a known test tube or centrifuging tube. In the latter case, the rigid stop for the piston is formed by an annular shoulder which is formed in the end wall and which surrounds the piston extension.

Preferably, care is taken that the piston cannot be pushed to a location closely below the end wall carrying the connection piece, as is generally the case in known blood extraction devices. On the contrary, when the piston is in its pushed-in state, there should be a buffer space between the piston and the closure member carrying the connection piece, the magnitude of the buffer space being between 5% and 30%, preferably 15% of the maximum interior space of the device when the piston rod is fully retracted. Thus, even when the piston rod is withdrawn rapidly, the buffer action of the air in the said space minimizes the vacuum which acts upon the blood drawn in and which would otherwise cause the blood to foam up and thus adversely affect the blood.

Furthermore, the space at the top end of the cylinder is also suitable for accommodating sufficient quantities of certain substances, such as substances for inhibiting coagulation of the blood, so that the blood drawn in immediately comes into contact with these substances.

The buffer space existing when the piston rod is in its pushed-in state is created preferably by means of a stop formed by a thickened portion at the free end of the piston rod.

Furthermore, it is proposed to provide on the end of the piston remote from the piston rod one or a plurality of projections distributed around the periphery, and to provide in the handle at the end of the piston rod one or a plurality of bores distributed around the periphery. These projections and bores permit the piston and the piston rod to be screwed to one another mechanically after the piston rod has been inserted into the cylinder and the piston has been inserted from the other end of the cylinder.

The cannula connection on the closure member is arranged preferably eccentrically of the central axis of the cylinder, and the closure member overlaps the cylinder and is screwed onto the end of the latter.

Preferably, the closure member is of special construction for the reasons given hereinafter. A collar projects axially from the closure member and is arranged coaxially of the cylinder. The collar is closed by means of an end wall which carries the cannula connection and whose periphery is provided with a radially projecting bead. This collar, together with the bead, permits the insertion of the blood extraction device into one of the two retaining forks of an automatic device for loading the blood extraction device, while the other retaining fork engages behind the handle at the end of the piston rod. Furthermore, the collar and the bead enable the blood extraction device to be rotated after it has been inserted into the aforesaid automatic device. Thus, the cannula mounted on the eccentrically arranged cannula connection can be brought into its bottommost position, i.e. closely above the vein to be punctured.

The cannula connection is a tubular member which projects axially parallel from the end wall and which is remote from the cylinder and tapers conically outwardly and permits the mounting of the known cannulae having a substantially funnel-shaped connection piece.

In another preferred construction, the cannula connection is a tubular member which extends axially parallel from the end wall towards the cylinder and which has a conically tapering bore. In this case, either a double conical intermediate member is necessary if it is desired to use the known cannulae, or cannulae having an externally conical connection plug are used.

Advantageously, the periphery of the connection piece is milled in order to facilitate the screwing-on or screwing-off of the connection piece.

In order to be able to seal the cannula connection after the blood sample has been removed and after the cannula has been removed, a closure cap is provided which can be mounted onto the closure member and which is provided with a counter-member for sealing the cannula connection in an air-tight manner. According to the construction of the connection piece, this counter-piece is either a collar having a conical bore, or a conical projection. In order to interconnect the closure cap and the closure member so as to be non-rotatable relative to one another, a cup-like recess, disposed eccentrically of the axis of the cylinder, is provided in that side of the end wall of the closure member which faces the closure cap. A projection forming a counter-member for the cup-like recess is located in the closure cap and can engage the cup-like recess upon mounting the closure cap.

This closure cap enables work to be carried out in a clean manner, and, when unscrewing the closure cap from the cylinder, prevents the operator's fingers from coming into contact with blood located in the cannula extension. This is very important, particularly when processing infectious blood.

When the closure cap has been mounted onto the closure member, these two parts form a unit and can be commonly screwed off the cylinder without the risk of coming into contact with the blood which has been extracted.

Compared with the known blood extraction devices having a plug, the screw connection of the closure cap also offers the advantage of a clean mode of operation without the operator running the risk of infection. Namely, when removing the plug inserted into the end of the cylinder, even when working carefully, it is difficult to prevent small drops of blood from being flung out of the cylinder, the personnel then running the risk of infection. This risk exists particularly in mass operation in modern hospitals and research institutes. The screw closure enables work to be carried out in a careful and clean manner without the risk of spilling drops of blood.

Preferably, the closure cap, which is made from resilient plastics material, has on the inside of its open edge an annular bead which locks behind the annular bead on the closure member when the latter is mounted and prevents the closure cap from dropping off. The length of the aforementioned projection on the closure cap is such that it enables the two annular beads to engage only when the closure cap and the closure member are in the correct position relative to one another and the projection can engage into the cup-like recess.

In this construction of the closure member having an outwardly projecting, conical tubular member acting as the cannula connection, it is further proposed that the projection in the closure cap, forming the rigid connection, be of hollow construction, the end entering the cup-like recess being closed, and the other end, located at the closed end of the cap, being open. This opening in the projection is conical and, after turning round the closure cap, enables the tubular member to be temporarily closed in a leakproof manner, without a lock connection being established between the closure member and the closure cap.

Preferably, the periphery of the closure cap is also milled, thus facilitating the unscrewing of the two parts from the cylinder of the blood extraction device after the closure cap has been mounted onto the closure member.

In the case of a closure member which has an inwardly extending conical tubular member for receiving a cannula, and in accordance with a further development of the invention, the collar of the closure member also extends into the cylinder, extends axially beyond the tubular member, and one of its end faces is closed by means of a tearable foil. A substance influencing the coagulation of the blood, such as a coagulation inhibitor, can then be accommodated in this space sealed by the foil. As soon as the cannula is mounted, the connection piece, which extends axially beyond the tubular member and the collar in the closure cap, pierces the foil and allows the liquid or solid substance to enter the cylinder of the blood extraction device where it is mixed with the blood which has been extracted.

In order to prevent the egress of such a substance even when the closure cap has been removed, the tubular member is preferably closed either by the foil mounted on the top of the end wall of the closure cap or by a foil which is mounted on its inner free end and which is torn when inserting the cannula. If such a substance is to be added to the blood which has been extracted, this substance can also be introduced into the interior of the cylinder. If the closure member is provided with an outwardly projecting tubular member, it is advantageous to close the free end of the tubular member by means of a tearable foil.

It is further proposed to provide in the top of the closure member a recess for receiving a substance of this type. The top of this recess is closed by a tearable foil and its bottom end communicates with the interior of the blood extraction device by way of a narrow opening. In particular, such a recess can accommodate a sequestering agent of solid or pasty consistency whose specific weight lies between the specific weight of the blood cake produced upon centrifuging and the specific weight of the serum. The opening at the underside of the recess is sufficiently narrow to prevent the pulverulent or pasty sequestering agent from entering the interior of the cylinder from the recess in the first instance. An increased force is then exerted upon the sequestering agent during centrifuging and forces the sequestering agent into the cylinder through the narrow opening, the closure foil at the same time being ruptured.

The above-mentioned venting of the space, located between the piston seal on the one hand and, on the other hand, the zone of contact between the piston extension and the annular sleeve, is important for the following reason;

When the piston is in its retracted state, air is located in this space and the blood sample which has been drawn in is located above the piston seal. Considerable pressure differences occur at the lip seal of the piston upon centrifuging the blood sample and, in one case or the other, might result in a certain quantity of blood entering the aforementioned air space. The air located in the space is at the same time correspondingly compressed. The piston ceases to be loaded by pressure after the centrifuging operation has been completed, and there is the risk that the air which is enclosed in the said space, and which is still compressed, will expand by virtue of the fact that a portion of the air will escape upwardly as a result of a slight leak in the lip seal of the piston. The air bubbles then enter the blood cake and, in the most unfavourable case, can throw red blood corpuscles from the blood cake into the serum located thereabove, the serum thus being rendered unusable for further examination.

Thus, in accordance with the invention, the aforesaid space is to be vented towards one end or the other.

In one embodiment, venting is effected in the zone of contact between the piston extension and the annular sleeve receiving and retaining the piston extension, through one or a plurality of grooves which are disposed in the piston extension and/or in the end wall and the annular sleeve. If, in such a construction of the device, the lip seal of the piston should develop a leak during the centrifuging operation, excess pressure would not build up in the said space, since communication with the atmosphere is established by way of the said grooves. Consequently, there is no risk that the red blood corpuscles would be thrown from the blood cake into the serum even after the centrifuging operation has been completed.

In another construction of the device, the venting of the space is effected at the piston seal itself. The piston seal is leakproof in the first instance, that is when blood is being extracted by retracting the piston, and is opened only shortly before reaching the rigid stop at the end of the stroke of the piston. For this purpose, one or a plurality of ribs are provided on the inside of the cylinder closely above the shoulder acting as a rigid stop for the piston, which ribs raise the sealing lip of the piston from the inside wall of the cylinder when the piston is in this position.

Thus, in this construction, a leak is intentionally created between the sealing lip of the piston and the cylinder wall when the piston is in its retracted end position, while the piston extension sealingly engages into the surrounding annular sleeve. During centrifuging, a larger or smaller quantity of blood is forced into the said space by the raised sealing lip and, during the centrifuging operation, the air located in the space is forced out upwardly and escapes upwardly through the blood. After the centrifuging operation has been completed, the said space no longer contains air which might escape upwardly and entrain red blood corpuscles.

In both methods of venting, an annular chamber is provided around the annular sleeve below the underside of the piston and can receive particles of fluid which, during the centrifuging operation, inadvertently pass through the lip seal or, in the other embodiment, intentionally pass through the lip seal. Preferably, the annular chamber is such that its top boundary surface slopes upwardly and outwardly.

In the first method of venting through grooves in the piston extension and in the annular sleeve receiving the piston extension, the aforementioned annular chamber ensures that the generally only small quantity of blood which has unintentionally passed through the lip seal of the piston during the centrifuging operation remains in the annular chamber and does not drift downwardly from the blood extraction device. This also renders it possible to work in a clean manner without the risk of infection.

The blood extraction device in accordance with the invention involves special sealing problems by virtue of the fact that, when extracting the blood, only a relatively small pressure difference prevails on each side of the lip seal of the piston in the first instance, although considerable pressure differences occur in the opposite direction at the lip seal when centrifuging with the high centrifugal forces which are normally used.

To ensure that the sealing lip of the piston abuts firmly against the cylinder wall during the centrifuging operation, it is proposed to provide the top of the piston with a cup-shaped cylindrical recess whose diameter is such that the collar which surrounds the cavity, and whose free edges have an external circular sealing bead or sealing lip, is thin and resilient. By virtue of this measure, the high pressure occurring during the centrifuging operation exerts forces in a radial direction as well as forces in an axial direction, which radial forces then press the sealing bead on the thin and resilient collar firmly against the cylinder wall.

Preferably, the thickness of the disc carrying the thin collar is such that the disc is virtually non-resilient. This prevents the forces occurring during centrifuging from deforming the piston to an extent where the seal around the periphery of the collar is impaired. In particular, such a construction of the bottom of the piston renders it possible to dispose the aforementioned cavity below the piston which, when in its retracted position, now abuts inwardly against the top edge of the annular sleeve on the one hand and, on the other hand, outwardly against the annular shoulder, without flexing between these two annular support surfaces.

A further proposal is that the inner surface of the collar of the piston widens conically towards the free end of the piston and tapers towards the wall of the cylinder. Thus, the formation of any gaps between the collar and the cylinder wall on the side of the higher pressure is precluded from the outset.

The invention will now be further described by way of example, with reference to the accompanying drawings, in which.

The same reference numerals are used for the parts or corresponding parts throughout the Figures, although they carry different indices "a" to "m" for the purpose of distinguishing between the different embodiments.

Figure 1:
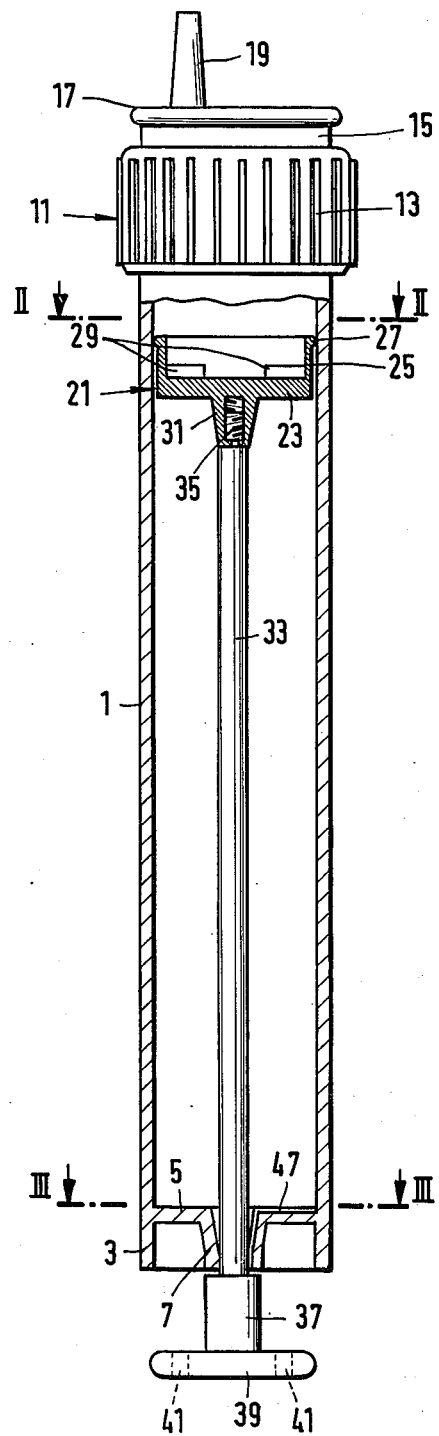
FIG. 1 is a partially sectioned illustration of one embodiment of a blood extraction device constructed in accordance with the present invention.
Figure 2:
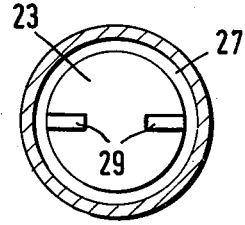
FIG. 2 is a section taken on the line II—II of FIG. 1.
Figure 3:
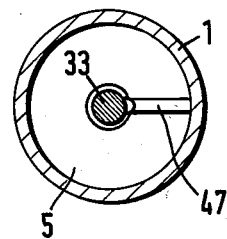
FIG. 3 is a section taken on the line III—III of FIG. 1.

The blood extraction device illustrated in FIGS. 1 to 3 is made entirely from plastics material, a transparent, hard plastics material having been used for the cylinder 1, and a somewhat softer plastics material having been used for the piston. The rear end of the cylinder 1 is closed by means of a planar end wall 5, although the rear end of the cylinder extends beyond the end wall 5 to form a stand ring 3. The end wall 5 has a central bore through which the piston rod 33 passes, and an annular sleeve 7 which surrounds the central bore and which is constructed so as to widen towards the interior of the cylinder in a conical manner. A piston 21 is displaceably guided in the cylinder 1 in an airtight manner and comprises a bottom disc 23 and a thin, resilient collar 25 which is carried by the disc 23 and whose free edge carries an external sealing bead 27. An extension 31, formed integrally with the bottom disc 23, projects from the side of the disc 23 remote from the collar 25 and has a screw-threaded bore for receiving the screw-threaded spigot 31 at the end of the piston rod 33. The extension 31 is of conical configuration externally and fits into the conical opening in the annular sleeve 7 when the piston is retracted. The angle of taper is chosen such that it is selflocking, so that the extension drawn into the annular sleeve is retained therein.

The rear end of the piston rod, extending out of the cylinder, is provided with a thickened portion 37 and a handle 39 contiguous thereto. The thickened portion forms a stop when advancing the piston rod, the piston rod being dimensioned such that a buffer space, equal to 15% of the maximum interior space when the piston rod is fully retracted, remains in front of the piston 21 when the latter is in its pushed-in state.

Two radially extending projections 29 are located above the bottom disc and within the collar 25 of the piston and, in conjunction with two bores 41 in the handle 39, enable the piston rod to be screwed mechanically to the piston inserted from the other end.

The end wall 5 and the surrounding annular sleeve 7 have a venting groove 47 (also see FIG. 3).

The front end of the cylinder 1 is closed by means of a screwed-on closure member 11. The outer surface of the closure member has a milled portion 13 which facilitates the screwing-on and the screwing-off of the closure member.

The closure member has a collar 15 and, contiguous thereto an end wall having a radially projecting bead 17. The end wall carries, eccentrically of the cylinder axis, a conical tubular member 19 acting as a cannula extension for mounting the connection piece of a cannula.

Figure 4:
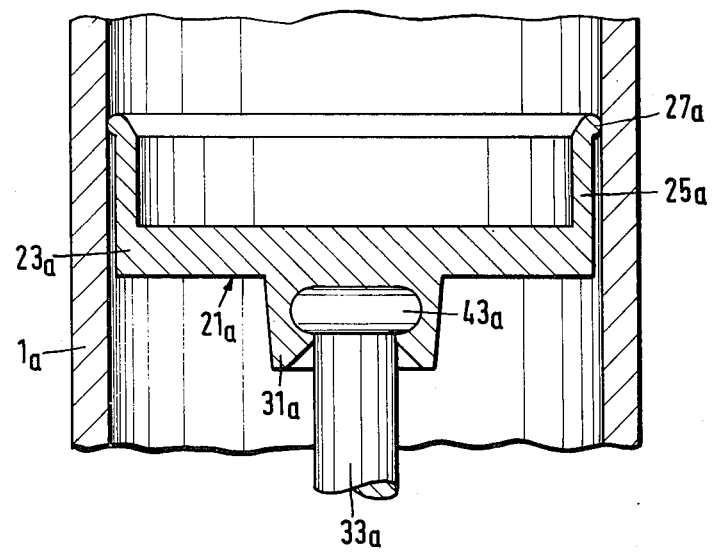
FIG. 4 is a fragmentary section, drawn to an enlarged scale, through the piston of another embodiment of blood extraction device constructed according to the present invention.

As is shown in FIG. 4, a locking connection can be used instead of screwing the piston rod to the piston extension. The piston 21a guided in the cylinder 1a again has a cylindrical bottom disc 23a, a thin collar 25a having a sealing bead 27a, and a conical extension 31a which, in the present instance, has a complementary recess for receiving the thickened end 43a of the piston rod 33a. Since the piston 21a is made from a resilient plastics material, the thickened end 43a of the piston rod can be snapped into the extension 31a without difficulty.

Figure 5:
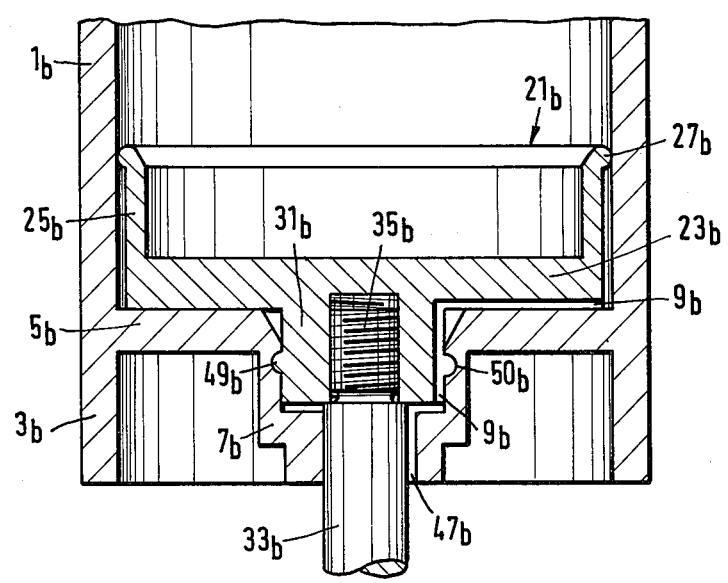
FIG. 5 is a fragmentary section, drawn to an enlarged scale, through the rear end of a further embodiment of a blood extraction device; constructed according to the present invention.

In the modified embodiment illustrated in FIG. 5, a cylindrical annular sleeve 7b is provided in the end wall 5b of the cylinder 1b and receives the extension 31b of the piston 21b which is also of cylindrical configuration externally. The annular sleeve 7b incorporates an annular groove 50b into which a complementary annular bead 49b on the periphery of the extension 31b engages when the piston 21b is in its rear end position defined by the end wall 5b. The annular chamber between the collar 25b and the cylinder 1b is vented by means of a groove 9b which leads radially inwardly in the underside of the bottom disc 23b and then extends radially downwardly along the outer surface of the extension 31b, and a further groove 47b in the annular sleeve 7b. The two grooves communicate with one another by means of an annular chamber which is produced by virtue of the fact that the piston extension 31b, when in the illustrated retracted position, is somewhat shorter than the interior surface of the annular sleeve 7b which surrounds the piston extension.

Figure 6:
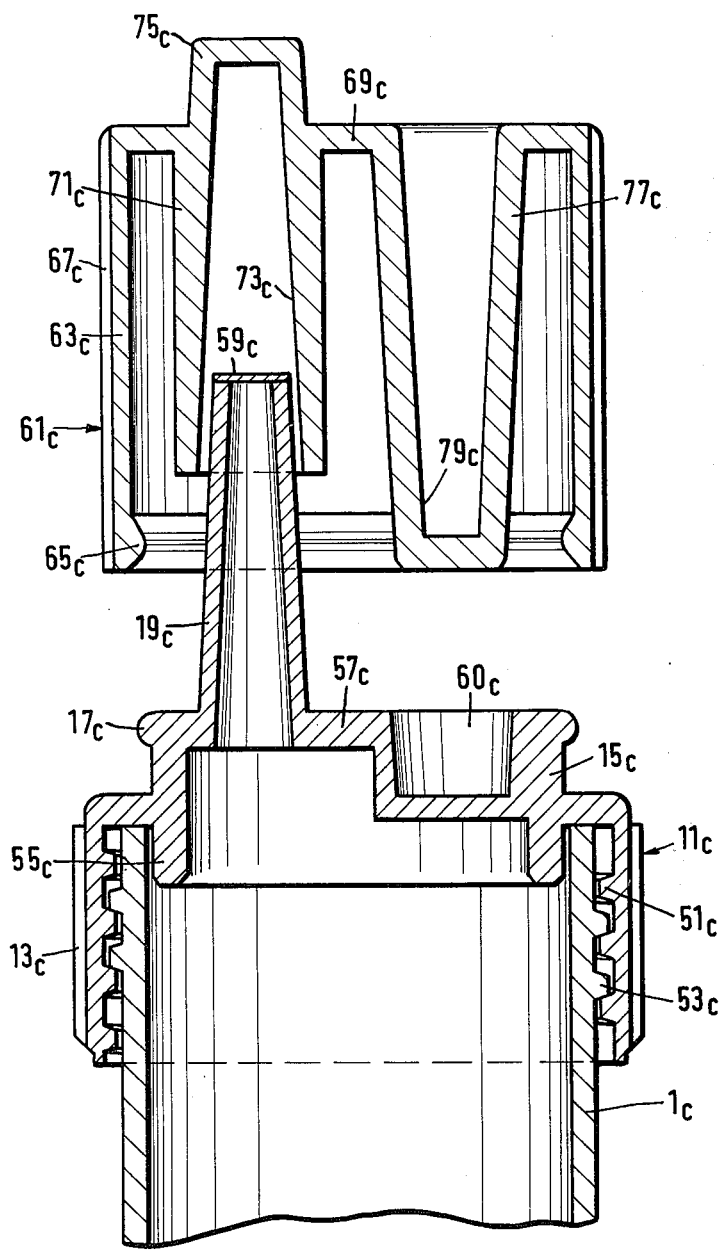
FIG. 6 is a fragmentary section, drawn to an enlarged scale, through the front end of the blood extraction device of FIG. 1.

The closure member 11c illustrated in FIG. 6 is of cap-like construction and has an internal screw thread 51c which is screwed into the external screw thread 53c at the end of the cylinder 1c. A collar 15c projects from the closure member 11c in an axial direction and is closed by means of an end wall 57c whose periphery is provided with a bead 17c which projects radially beyond the collar. An interior extension 55c of the collar extends into the cylinder 1c. A cup-shaped conical recess 60c is located in the end wall 57c of the closure member and is disposed eccentrically of the axis of the cylinder. The externally conical cannula extension 19c also projects from the end wall 57c eccentrically of the axis of the cylinder and its outer end is sealed by means of a tearable foil 59c.

The closure cap 61c associated with the closure member has a cylindrical outer surface 63c and an end wall 69c from which a tubular projection 71c having a conical bore 73c extends inwardly but is shorter than the outer surface 63c of the closure cap. An annular bead 65c is located internally at the bottom free end of the outer surface 63c of the closure cap, the exterior of the closure cap also being provided with a milled portion 67c to facilitate manipulation.

Furthermore, a projection 77c of internal and external conical construction extends from the end wall 69c of the closure cap into the closure cap and extends up to the free end of the wall 63c of the cap. This projection is arranged and dimensioned such that it engages into the cup-shaped recess 60c upon mounting the closure cap 61c onto the closure member 11c. Thus, the closure member 11c and the closure cap 61c are interconnected by means of the two eccentric projections so as to be non-rotatable relative to one another and are interconnected axially by means of the annular beads.

The bore 79c in the projection 77c is of conical configuration and permits closure of the cannula extension 19c when the closure cap is reversed, without axial locking by means of the annular beads. A rigid connection is then formed by a projection 75c which is formed on the end wall 69c and which engages into the recess 60c.

Figure 7:
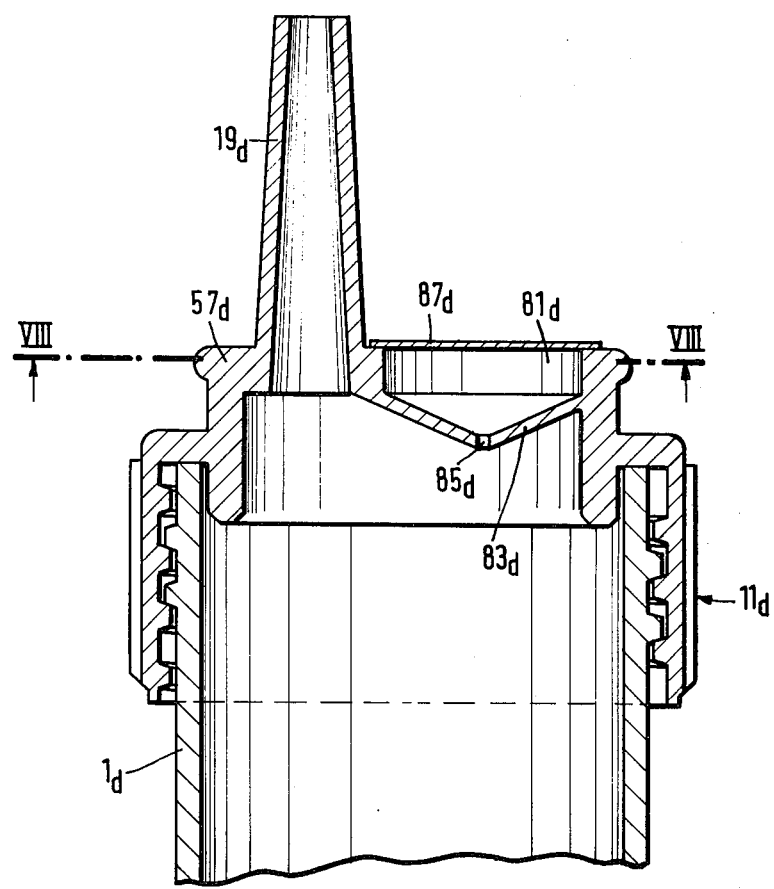
FIG. 7 is a section through the front end of a modified embodiment of the blood extraction device, similar to FIG. 6, in accordance with the invention.
Figure 8:
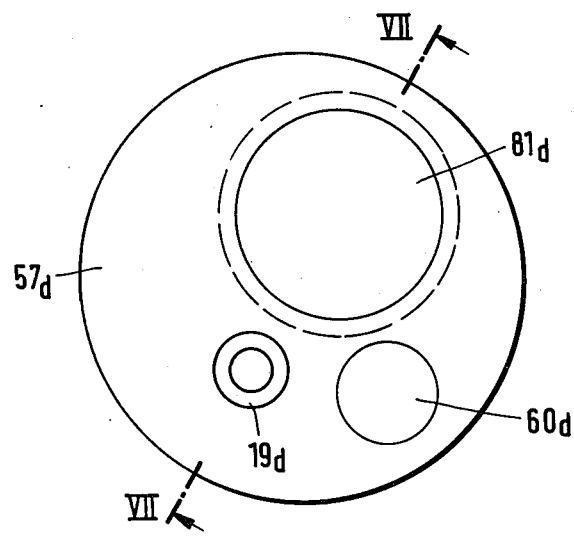
FIG. 8 is a section taken on the line VIII—VIII of FIG. 7.

In the modified construction of the closure member in accordance with FIGS. 7 and 8, a further recess 81d for receiving a pulverulent or pasty substance is provided in the end wall 57d in addition to the cannula extension 19d and the cup-shaped recess 60d. The top of the recess is sealed by means of a tearable foil 87d, and the bottom of the recess has a narrow opening 85d at the lowest point of the funnel-shaped partition 83d.

Figure 9:
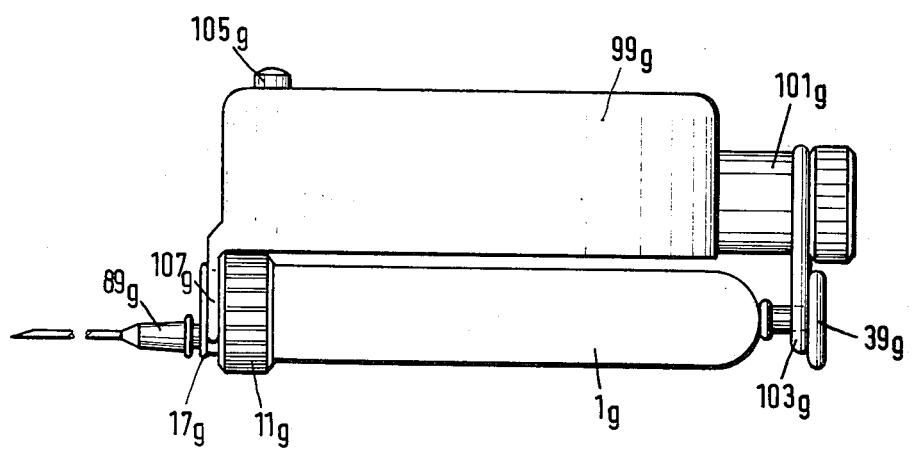
FIG. 9 is a side elevation of a blood extraction device, in accordance with the invention, which is inserted into an automatic device for loading.

The automatic device, illustrated in FIG. 9, for loading the blood extraction device is known per se and is only illustrated diagrammatically and comprises a main body 99g having at its front end a retaining fork 107g and a release knob 105g, and a displaceable piston 101g which has a retaining fork 103g and which extends out of the housing. The retaining fork 107g engages into the collar of the closure member 11g behind the bead 17g, while the retaining fork 103g engages into the thickened end of the piston rod in front of the handle 39g. Thus, the cylinder 1g, together with the closure member and the mounted cannula 89g, is rigidly connected to the housing 99g of the automatic device, while, after actuating the knob 105g, the piston 101g slowly retracts the handle 39g and thus the piston rod and the piston by means of the retaining fork 103g.

Figure 10:
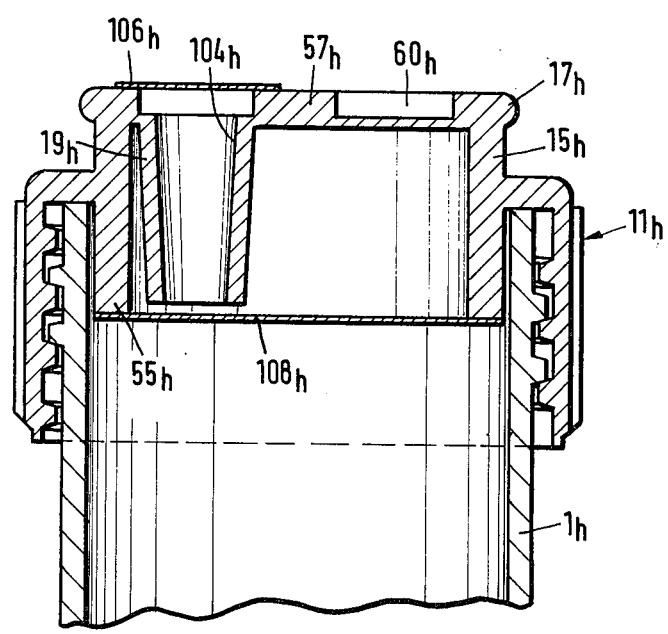
FIG. 10 is a fragmentary section, drawn to an enlarged scale, through the front end of a blood extraction device according to the present invention, having a modified closure member.

In the construction of the closure member of FIG. 10, the underside of the collar 55h extending into the cylinder 1h is sealed by means of a tearable foil 108h. Furthermore, the conical bore 104h in the tubular cannula connection 19h is also sealed by means of a tearable foil 106h. The two foils are ruptured upon inserting the conical plug of a cannula and then allow a substance previously located in the chamber sealed by the foils, and which is required during the relevant examination of the blood, to enter the interior of the cylinder 1h.

Figure 11:
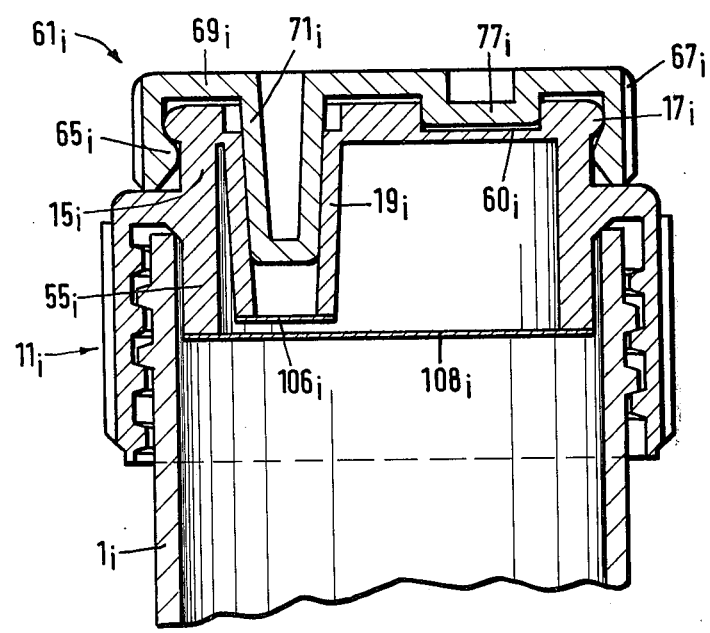
FIG. 11 is a section through the front end of a blood extraction device according to FIG. 10, a closure cap being placed in position.

In the modified embodiment illustrated in FIG. 11, the collar 55i of the closure member 11i is again sealed at its bottom end by a tearable foil 108i, while the inner free end of the tubular cannula extension 19i is sealed by means of a tearable foil 106i.

The closure cap 61i illustrated in FIG. 11 again has at its open edge an annular bead 65i for engaging into the outer annular bead 17i on the closure member, while a conical projection 71i for sealing the cannula extension 19i extends inwardly from the end wall 69i of the closure cap, and a projection 77i is provided for engaging into the cup-shaped recess 60i in the closure member.

Figure 12:
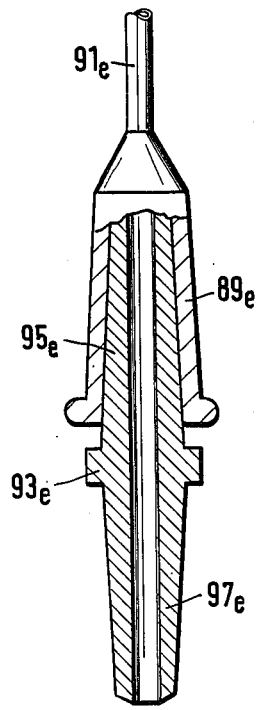
FIG. 12 is a fragmentary section through a conventional cannula with inserted intermediate member for attachment to a closure member.

FIG. 12 shows an intermediate member 93e having a respective cone 95e and 97e at each side, the intermediate member being used to mount a conventional cannula 91e, having a funnel-shaped connection piece 89e, onto a closure member in accordance with FIG. 10.

Figure 13:
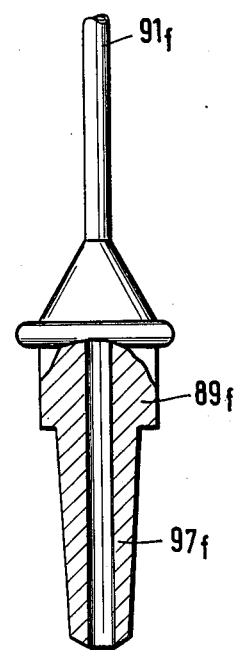
FIG. 13 is a fragmentary section through a modified cannula.

FIG. 13 shows a cannula 91f which is already provided with a connection piece 89f having a cone-shaped portion 97f for insertion in conical bore 104h (FIG. 10).

Figure 14:
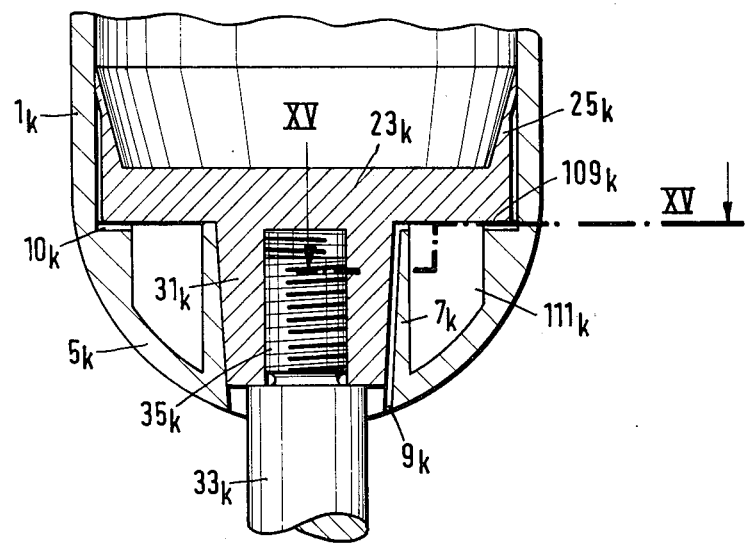
FIG. 14 is a fragmentary section through the rear end of a still further embodiment of a blood extraction device constructed in accordance with the present invention, having a circular bottom and venting at the piston extension.

In the embodiment of FIG. 14, the hemispherical end wall 5k contiguous to the cylinder 1k has a thickened portion which forms an annular shoulder 109k for the bottom disc 23k of the piston. Furthermore, the piston has a thin, resilient collar 25k which tapers towards its free end where it forms a sealing lip.

Two diametrically opposite radial grooves 10k are located in the annular shoulder 109k for the purpose of venting the annular gap between the collar 25k and the cylinder 1k, and connect the aforesaid gap to a cavity 111k.

The extension 31k of the piston has an external conical configuration and engages in a self-locking manner in the annular sleeve 7k which is also provided with a conical bore. In this instance, for the purpose of venting, a groove 9k extending in the longitudinal direction of the annular sleeve 7k is provided in the latter and connects the annular chamber 11k to the atmosphere.

The end of the piston rod 33k has a screw-threaded spigot 35k which is screwed into a complementary screw-threaded bore in the extension 31k.

Figure 15:
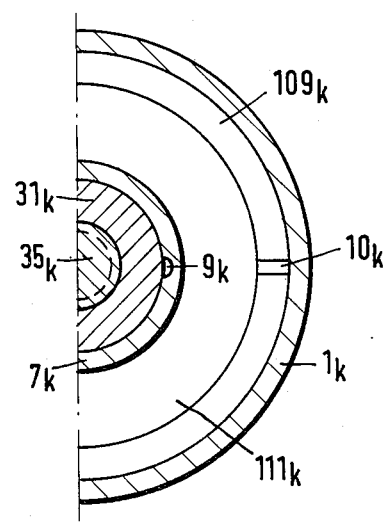
FIG. 15 is a section taken on the line XV—XV of FIG. 14.
Figure 16:
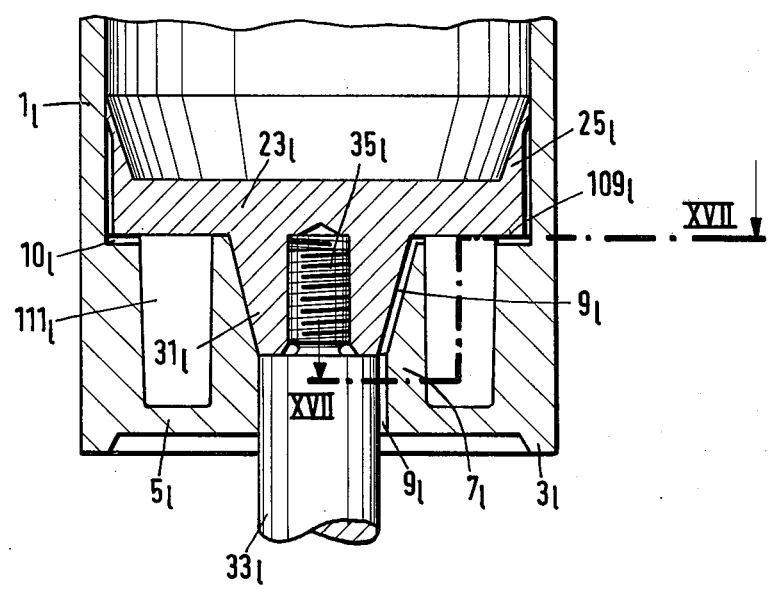
FIG. 16 is a section, similar to FIG. 14 through the rear end of a still further embodiment of a blood extraction device constructed in accordance with the present invention, having a disc-shaped end wall and stand ring.
Figure 17:
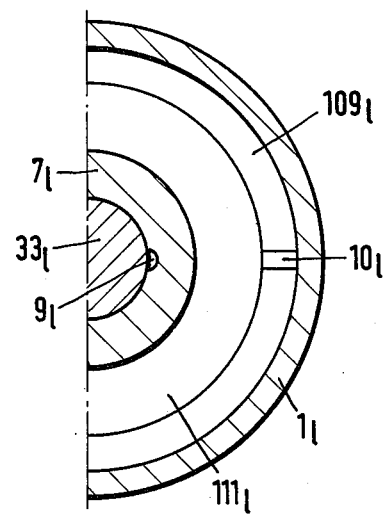
FIG. 17 is a section taken on the line XVII—XVII of FIG. 16.
Figure 18:
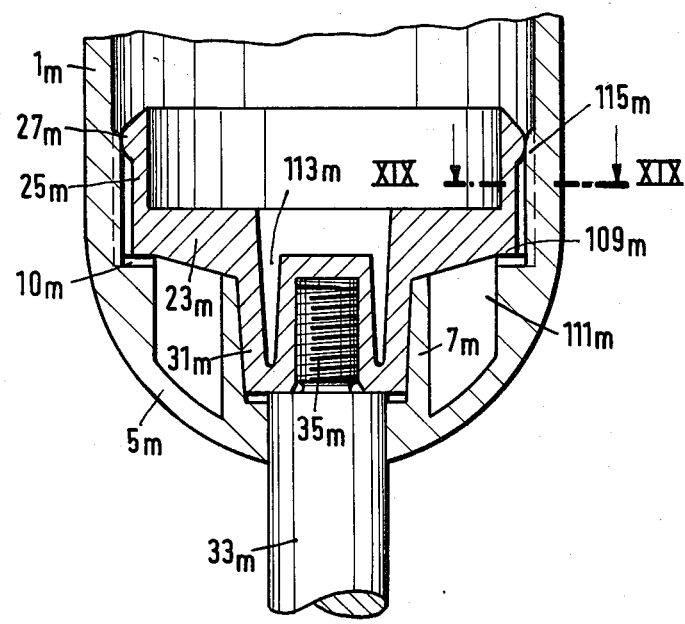
FIG. 18 is a section similar to FIG. 14, through the rear end of a still further embodiment of a blood extraction device constructed in accordance with the invention, having a different type of venting.
Figure 19:
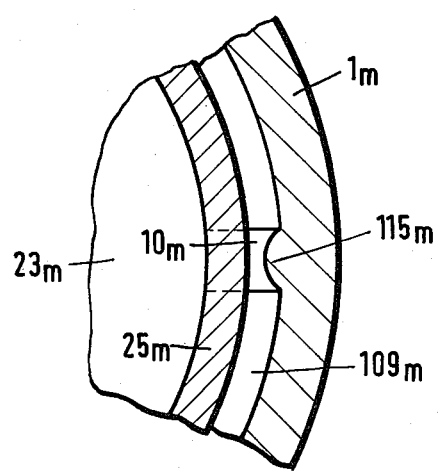
FIG. 19 is a fragmentary section taken on the line XVIV—XVIV of FIG. 18.

In the embodiment illustrated in FIGS. 16 and 17, the cylinder 1l has a disc-shaped end wall 5l having a stand ring 3l and, like the embodiment shown in FIGS. 14 and 15, is vented by a groove 9l in the conical seat of the extension 31l in the annular sleeve 7l. Here also, the wall of the cylinder 1l has a thickened portion whose upper end forms an annular shoulder 109l. This annular shoulder is again vented towards the annular chamber 111l by means of radial grooves 10l. In the embodiment illustrated in FIG. 18, which again has a spherical end wall, the annular gap between the collar 25m of the piston and the cylinder 1m is vented at the sealing lip 27m of the collar 25m. Here also, the hemispherical end wall 5m is provided with a thickened portion whose top end forms a shoulder 109m on which the bottom disc 23m of the piston is supported. The shoulder is again vented towards the annular chamber 111m by radial grooves 10m.

Ribs 115m project inwardly from the wall of the cylinder 1m above the annular shoulder 109m. The length of the ribs is such that, upon retracting the piston, the sealing bead 27m slides onto the ribs 115m only shortly before the piston reaches the rigid stop on the shoulder 109m, the sealing bead 27m thus being raised from the wall of the cylinder to effect the venting operation. The underside of the bottom disc 23m of the piston extends conically, i.e. upwardly and outwardly, so that any air bubbles in the annular chamber 111m do not remain therein but, during the centrifuging operation, are forced by way of the grooves 10m and the released lip seal 27m into the chamber located thereabove.

In this embodiment, the conical extension 31m seals in the annular sleeve 7m. The end of the piston rod 33m carries a screw-threaded spigot 35m which is screwed into a complementary screw-threaded bore in the extension 31m. In order to avoid impairing the conical outer surface of the extension of the piston made from plastics material by non-uniform shrinkage in the region of the screw threads, an angular gap is incorporated in the extension which separates the cup-shaped inner part, provided with a screw-threaded bore, from the outer part carrying the conical wall which engages the inner wall of annular sleeve 7m. Reliable sealing is thus ensured.

I claim:

1. A device for extracting blood, the device comprising a cylinder having a first end and a second end, a removable closure member at said first end of said cylinder and a fixed end wall at said second end of said cylinder, a connection means for a cannula carried on said closure member, a piston guided in said cylinder in an air-tight manner, a piston rod guided in a central bore in said fixed end wall, an extension of said piston for releasably receiving said piston rod provided on that end of said piston remote from said closure member, said fixed end wall forming a rigid stop for said piston in its retracted position, an annular sleeve means concentrically surrounding said central bore provided on said fixed end wall for receiving and retaining said extension of said piston, and vent means in the space between at least one point at which said piston engages said cylinder and a zone of contact between said extension of said piston and said annular sleeve for venting the device when said piston is in its retracted position, said vent means extending along the surfaces of said fixed end wall and the bottom wall of said piston and further extending between the surface of said piston extension and said annular sleeve.

2. A device according to claim 1, wherein the annular sleeve in the end wall and the extension, on the piston are of conical construction, the angle of taper being such that self-adhesion is ensured.

3. A device according to claim 1, wherein said annular sleeve and said extension of said piston are of cylindrical construction and are provided with a stop bead and a stop groove for retaining said piston in its retracted position.

4. A device according to claim 1, wherein said fixed end wall is of virtually disc-shaped construction and its side remote from the cylinder is provided with a cylindrical stand ring.

5. A device according to claim 1, wherein the end wall is of hemispherical construction.

6. A device according to claim 5, wherein an annular shoulder which is formed in the end wall and which surrounds the piston extension, forms said rigid stop.

7. A device according to claim 1, wherein when said piston is in its pushed-in state, there remains between said piston and said closure member carrying said connection means a buffer space whose magnitude is between 5% and 30% of the maximum interior space of the device when said piston rod is fully retracted.

8. A device according to claim 7, wherein said buffer space comprise substantially 15% of the maximum interior space of the device.

9. A device according to claim 7, including a stop on an end of said piston rod which projects from said cylinder for limiting maximum travel of said piston in an inwardly direction.

10. A device according to claim 1, wherein one or a plurality of circumferentially distributed projections are provided on the end of the piston which is remote from the piston rod, and one or a plurality of circumferentially distributed bores are provided in the handle at the end of the piston rod and permit the piston rod and the piston to be mechanically screwed to one another after the piston rod has been inserted into the cylinder and the piston has been inserted on the other end of the cylinder.

11. A device according to claim 1, wherein said connection means for a cannula on said closure member is arranged eccentrically of the central axis of said cylinder.

12. A device according to claim 1, wherein said closure member overlaps said cylinder and is screwed onto said first end of the latter.

13. A device according to claim 11, including a collar which projects axially from said closure member and is coaxial of said cylinder and is closed by a second end wall, said second end wall carrying said connection means for a cannula, the periphery of said second end wall having a bead which projects radially beyond said collar.

14. A device according to claim 13, wherein said connection means for a cannula is a tubular member which projects axially parallel from said second end wall and which is remote from said cylinder and tapers conically outwardly and has a longitudinal bore passing therethrough.

15. A device according to claim 13, wherein said connection means for a cannula is a tubular member which extends from said second end wall, axially parallel to the axis of said cylinder and has a conically tapering bore.

16. A device according to claim 12, including a milled outer surface provided on the periphery of said closure member.

17. A device according to claim 12, including a closure cap mounted on said closure member, said cap having a counter-member for sealing said connection means for a cannula in an airtight manner.

18. A device according to claim 17, wherein said connection means is a tubular member having a conical wall, and said counter-member mounted on said closure cap is a collar having a conical bore which corresponds to said conical wall of said tubular member.

19. A device according to claim 17, wherein said connection means is a tubular member having a tapered bore and said counter-member mounted on said closure cap is a conical projection whose taper corresponds to the taper of said bore in said tubular member.

20. A device according to claim 17, including a cup-like recess disposed eccentrically of the axis of said cylinder in that side of said second end wall which faces said closure cap and a projection which extends from an end face of a said closure cap and which, when said closure cap is mounted, is in alignment with said recess and engages therein and interconnects said closure member and said closure cap so as to be non-rotatable relatively to one another but releasable from one another.

21. A device according to claim 20, wherein said connection means is a conical tubular member, and said projection from an end face of said closure cap is of hollow construction defining a conical opening which fits sealingly onto said conical tubular member.

22. A device according to claim 20, including a milled outer surface portion around the periphery of said closure cap.

23. A device according to claim 20, including a bead-like portion on the inside of an open edge of said closure cap made from plastics material, said bead-like portion locking behind an annular bead formed on said closure member when the latter is mounted.

24. A device according to claim 21, wherein the length of said annular bead is such that said annular bead enables said bead-like portion of said closure cap to engage behind said annular bead on said closure member only after said annular bead has entered the cup-like recess.

25. A device according to claim 24, wherein a collar also extends into the cylinder and extends axially beyond the tubular member a tearable foil closing the end face of the collar.

26. A device according to claim 25, wherein a tearable foil closes the tubular member, the tearable foil being mounted on the top of the end wall.

27. A device according to claim 25, wherein a tearable foil closes the inner free end of the tubular member.

28. A device according to claim 1 wherein a recess is provided in the closure member for receiving a sequestering agent for the blood fractions separated during centrifuging, the top of which recess is closed by a tearable foil and the bottom of the recess communicates with the interior of the blood extraction device by way of a narrow opening.

29. A device according to claim 1, wherein said vent means comprise at least one groove in said extension of said piston.

30. A device according to claim 1, wherein said piston has a cup-shaped, cylindrical recess defined by a peripheral collar and whose diameter is such that said collar has a free edge and defines a circular, thin and resilient sealing bead which contacts the interior surface of said cylinder.

31. A device according to claim 32, wherein the thickness of that portion of said piston carrying said collar is such that it is virtually non-resilient.

32. A device according to claim 1, wherein said piston has a collar whose internal surface widens conically towards the free end of the piston and tapers up to the wall of the cylinder.

33. A device according to claim 1, wherein said vent means comprise at least one groove in said annular sleeve.

34. A device according to claim 1, wherein said vent means comprise a plurality of grooves in said extension of said piston.

35. A device according to claim 1, wherein said vent means comprise a plurality of grooves in said annular sleeve.

36. A device for extracting blood, the device comprising a cylinder having a first end and a second end, a removable closure member at said first end of said cylinder and a fixed end wall at said second end of said cylinder, a connection means for a cannula carried on said closure member, a piston guided in said cylinder in an air-tight manner and having a sealing lip, a piston rod guided in a central bore in said fixed end wall, an extension of said piston for releasably receiving said piston rod provided on that end of said piston remote from said closure member, a portion of said fixed end wall forming a rigid stop for said piston in its retracted position, an annular sleeve means concentrically surrounding said central bore provided on said fixed end wall for receiving and retaining said extension of said piston, an annular chamber which surrounds the annular sleeve means below the underside of the piston and which serves to receive particles of fluid during a centrifuging operation, and wherein space between said piston sealing lip and the end of said piston extension is vented by means of at least one channel between a plurality of ribs which are located on the inside of said cylinder and which raise said sealing lip of the said piston from the interior wall of said cylinder and at least one further channel formed in said portion of said fixed end wall which provides communication between said annular chamber and the first said at least one channel.

37. A device according to claim 36, wherein the underside of the piston which annularly surrounds the extension is of conical construction such that the upper boundary of the annular chamber located below the piston slopes upwardly and outwardly.

* * * * *

UNITED STATES PATENT AND TRADEMARK OFFICE
CERTIFICATE OF CORRECTION

PATENT NO. : 4,057,050
DATED : November 8, 1977
INVENTOR(S) : Walter SARSTEDT

It is certified that error appears in the above-identified patent and that said Letters Patent are hereby corrected as shown below:

Column 4, line 53, after "advantageous" insert --also--

Column 12, line 27, delete "11" and insert --12--

Column 13, line 17, delete "21" and insert --23--

Column 14, line 1, delete "32" and insert --30--

Signed and Sealed this

Eighteenth Day of April 1978

[SEAL]

Attest:

RUTH C. MASON
Attesting Officer

LUTRELLE F. PARKER
Acting Commissioner of Patents and Trademarks